United States Patent [19]
Bolton et al.

[11] Patent Number: 5,286,760
[45] Date of Patent: Feb. 15, 1994

[54] PROCESS FOR REDUCING IMPURITY LEVELS IN METHYLENE DIPHENYAMINES

[75] Inventors: Jeffrey S. Bolton, Wheeling; Robert L. Mayen, New Martinsville, both of W. Va.

[73] Assignee: Miles, Inc., Pittsburgh, Pa.

[21] Appl. No.: 959,233

[22] Filed: Oct. 9, 1992

[51] Int. Cl.⁵ .................. C07C 263/10; C07C 265/12
[52] U.S. Cl. ..................................... 521/160; 521/185; 560/347; 560/358; 560/359; 564/330; 564/331; 564/332; 564/333; 564/334
[58] Field of Search ............... 564/330, 331, 332, 333, 564/334; 560/347, 358; 521/185, 160

[56] References Cited

U.S. PATENT DOCUMENTS

| | | | |
|---|---|---|---|
| 3,644,232 | 2/1972 | Bernard et al. | 564/333 |
| 4,094,907 | 6/1978 | Knofel et al. | 564/333 |
| 4,259,526 | 3/1981 | Dunlap et al. | 564/331 |
| 4,465,639 | 8/1984 | Hatfield, Jr. | 260/453 PH |
| 4,792,624 | 12/1988 | Hatfield, Jr. et al. | 564/333 |
| 4,952,611 | 8/1990 | Indyke | 521/128 |

*Primary Examiner*—Richard L. Raymond
*Attorney, Agent, or Firm*—Joseph C. Gil; Godfried R. Akorli

[57] ABSTRACT

Disclosed herein is a process for preparing a reaction product containing methylene diphenylamine comprising reacting aniline with an aldehyde, in the presence of a low level of an acid wherein the acid level is reduced before digesting reaction mixture at a high temperature which is sufficient to effect a rearrangement of the intermediates to produce a reaction product containing methylene diphenylamines and low levels of impurities.

16 Claims, No Drawings

PROCESS FOR REDUCING IMPURITY LEVELS IN METHYLENE DIPHENYAMINES

FIELD OF THE INVENTION

The present invention relates to the preparation of methylene di(phenylamines) having reduced levels of impurities. More specifically, the invention relates to a process for preparing methylene di(phenylamines) at high temperatures and low acid levels.

BRIEF DESCRIPTION of THE PRIOR ART

Generally, it is known in the art to react aniline with formaldehyde in the presence of an acid such as hydrochloric acid to produce polyamines. Of particular interest here is the use of the polyamines in the production polyisocyanates for use in the preparation of foams. Lately, the color of the foams has become one of the requirements for judging the quality of foams. Foams which are otherwise acceptable can be rejected because of dark color.

Impurities in the polyamines and consequently the polyisocyanates, at least in part, have been considered as the cause of discoloration in foams which are prepared with said polyisocyanates. Hence, research in this area has focused on the preparation of polyamines containing reduced amounts of impurities, U.S. Pat. No. 4,792,624 discloses that polymethylene polyphenyl polyisocyanates of improved color can be obtained from certain polyamines which are prepared by the following process. The process comprises the preparation of the corresponding polymethylene polyphenyl polyamine by condensing aniline and formaldehyde in the presence of an acid catalyst which is characterized by adding a minor proportion of a polyamine mixture comprising di(aminophenyl)methanes and oligomeric polymethylene polyphenyl polyamines, (collectively known as polymeric MDA) to an intermediate stage of the condensation reaction where the various intermediately formed aminobenzylamines are present.

U.S. Pat. No. 4,465,639 discloses addition of controlled amounts of water to the reaction mixture produced by phosgenation of a mixture of polymethylene polyphenyl polyamines (and the like polyamines produced by condensation of formaldehyde and aromatic amines) prior to complete removal of excess phosgene gives rise to the corresponding polymethylene polyphenyl polyisocyanates having significantly improved properties such color of the polyisocyanates.

U.S. Pat. No. 4,259,526 discloses a process for the preparation of mixtures of polyamines of the polyamino-polyaryl-polymethylene type whereby the proportion of the ortho-substituted products are substantially increased. This increase is brought about by adding the acid catalyst in two stages by reacting an aromatic amine with formaldehyde in the presence of an aqueous acid catalyst, or subjecting a condensate which has been obtained from an aromatic amine and formaldehyde in the absence of a catalyst to a first rearrangement in the presence of an aqueous acid catalyst, followed by adding aqueous acid catalyst to the resulting mixture, and the subjecting the mixture to a a rearrangement reaction at a temperature of 75 to 150 degrees Centigrade to obtain a condensation mixture containing the polyamines which are thereafter recovered.

By the present invention, there is provided a process for preparing polyamines having reduced amounts of impurities.

SUMMARY OF THE INVENTION

The present invention encompasses a process for preparing a reaction product containing methylene di(phenylamine) comprising reacting aniline with an formaldehyde, in the presence of an acid at a low level which is sufficient to catalyze the reaction at an initial and/or condensation stage of said reaction and to produce the methylene di(phenylamine) intermediates, providing a reaction mixture, at the condensation stage, with an acid content which is at or below the acid level hitherto or at the end of the condensation stage and holding the reaction mixture at the digestion stage at a high temperature which is sufficient to effect a rearrangement of the intermediates to produce the reaction product containing methylene di(phenylamines)and low levels of impurities.

In the present embodiment of the invention, the 2,4'-methylene diphenylamine isomer content is characteristically about 20 to 30 percent by weight based on the total content of the monomeric methylene di(phenylamine) (MDA). Generally, the 2,4-isomer content can range from lower values to up to 40 percent.

Definitions of some of the terms used herein are provided hereunder in the context of the claimed invention. By the term "initial stage" is meant the stage at which the aniline, formaldehyde and acid are brought together in a reaction vessel. As would be realized, the acid salt of the aniline can be reacted with the formaldehyde. As would also be realized, the process of this invention may entail split addition of the reagents. Typically, the reagents are brought together at a temperature of 10 to 100 degrees Centigrade and typically from about 70 to 80 degrees Centigrade.

By the term "condensation stage" is meant the stage at which aniline and formaldehyde react in the presence of an acid such as hydrochloric acid at a temperature range of 10 to 100 and typically from about 70 to 100 degrees Centigrade to form a reaction mixture containing intermediate aminobenzylamines and aminals.

By the term "digestion stage" is meant the stage at which the intermediate aminobenzylamines rearrange to form the reaction product containing methylene di(phenylamines) and polymethylene polyphenyl. Typically, the rearrangement takes place at about 100 to 250 degrees Centigrade, under pressure and typically from 35 to 1000 psi.

DETAILED DESCRIPTION OF THE INVENTION

In accordance with the invention, the reaction product containing methylene di(phenylamine) is characterized by low levels of impurities, particularly N-methyl methylene di(phenylamine) (N-methyl MDA) and/or acridane and acridine. Generally, the methylene di(phenylamine) can be prepared by reacting aniline with formaldehyde in the molar ratio of 1.5:1 to 15:1, in the presence of an acid such as hydrochloric acid.

In the present embodiment of the invention, the process for preparing the reaction product containing methylene di(phenylamine) comprises reacting aniline and formaldehyde in the presence of low levels of acid, partially neutralizing the acid at the condensation stage, and digesting the resulting mixture at high temperatures. The amount and type of the acid is that which is effective to catalyze the reaction and to produce intermediates of methylene di(phenylamine). Typically, the acid level is about 0.1 to 1 percent and preferably 0.18 to 0.22 percent by weight based on the weight of the reaction mixture. The acid can be added separately or in a mixture with aniline in a reaction vessel which is usually referred to as "a mix reactor". The useful acids can be the art-known acids disclosed in the prior art cited above. Suitable acids include water soluble acids having pKa values below 2.5 and preferably below 1.5. Specific examples include hydrochloric acid which is preferred, hydrobromic acid, sulfuric acid, triflouro acetic acid, methane sulfonic acid, phosphoric acid, acetic acid and the like.

The reaction at the initial stage typically takes place at a temperature of 10 to 100 and preferably 75 to 80 degrees Centigrade. The reaction can be monitored by various common analytical techniques such as gas chromatography or liquid chromatography. The condensation reaction between the aniline and formaldehyde is exothermic and if desired, the reaction mixture can be cooled in order to maintain it within the desired range. As would be realized, even though the stages of the process are recited distinctly, they can occur continuously and sometimes simultaneously one or more reaction vessels.

It is a distinct feature of the invention that the acid level of the reaction mixture is maintained at a low level at the end of the condensation stage. In contrast with art-related processes, the process of this invention, at the end of the condensation stage comprises reducing acid content from conventional levels. In accordance with this invention, the acid content of the reaction mixture can be maintained at, or reduced to a low level but effective level which is below the level at the end (including hitherto the end) of the condensation stage. By effective level is meant the level sufficient to produce substantial reaction and formation of intermediates as described herein. In the present embodiment of the invention, the acid level can be reduced to less than 1 percent and typically 0.06 to 0.1 percent by weight based on the total weight of the mixture. The reduction of the acid level can be effected by partial neutralization of the reaction mixture by, say, adding a base thereto in an amount sufficient to effect the required extent of reduction. The base can be added at a temperature of about 10 to 100 and typically from 90 to 95 degrees Centigrade, over a period of time sufficient to effect the desired neutralization. Typically this is done over a period of from 1 to 2 hours. Illustrative but non-limiting examples of the base can be sodium hydroxide, potassium hydroxide and the like.

The condensation stage of the reaction is typically but not necessarily conducted in a different vessel(s) to which the reaction mixture is conveyed. The reaction can be monitored by various art-known analytical methods. At the end of the condensation stage, the reaction mixture is admitted to the digestion stage. It is a distinct feature of the invention that the acid level is reduced before the reaction mixture is digested.

At the digestion stage, the reaction mixture with the reduced acid level is held at a high temperature of about 100 to 250 and preferably 100 to 230 degrees Centigrade, under pressure for a period of time sufficient to substantially complete the rearrangement to provide a product containing methylene di(phenylamine) and low levels of impurities. Typically, the digestion is conducted over a period of about 10 to 20 minutes. Within the above range, the particular temperature is a function of the period of heating. It is, however, a distinct feature of the invention that relative to the conventional digestion temperatures, the claimed process comprises subjecting the reaction mixture to a higher digestion temperature range. This stage of the reaction can be monitored by routine analytical procedures. When the process is considered complete, the resultant mixture comprising methylene di(phenylamine)is recovered by art-known techniques. For example, the resulting mixture can be neutralized and phase-separated.

Surprisingly, it has been found that by the process of this invention, there is obtained a reaction product containing methylene di(phenylamine)having low levels of impurities, particularly N-methyl MDA and/or acridane and acridine.

In the practice of the invention, the polyamines can be used in the preparation of lighter color polyisocyanates by the reaction of phosgene with the polyamine corresponding to the desired polyisocyanates. The phosgenation reaction can be conducted in the presence of an inert solvent such as chlorobenzene. The polyamines are reacted with phosgene in molar ratios of 1.5 to 20 moles and preferably about 2.2 to 4.0 moles of phosgene per amine group. Upon completion of the phosgenation, the excess phosgene and hydrogen chloride formed are separately or simultaneously removed.

In turn, the lighter color polyisocyanates can be used in the preparation of lighter color foams. In the preparation of the foams, the polyisocyanates are reacted with an active hydrogen-containing material in the presence of a blowing agent such carbon dioxide derived from the reaction of an isocyanate with water. Typically, art-known additives and auxiliary agents are employed in the preparation of the foams.

The invention is further described by the following non-limiting examples.

EXAMPLES

Example 1A

To a properly equipped reaction vessel was charged 3750 kg/hr of aniline and 690 kg/hr formaldehyde (37% aqueous solution) and 8.7 kg/hr of hydrochloric acid ( 36% aqueous solution) and reacted at 80-95 degrees Centigrade. The resultant mixture having an acid content of 0.195% by weight was then transferred to a different reaction vessel. Thereafter, the reaction mixture was neutralized by adding 4.6 kg/hr sodium hydroxide over 2 hours at 95 degrees Centigrade to reduce the acid level to 0.10 weight percent. The resultant mixture was then transferred to another vessel (digester) where it was maintained at 100–250 degrees Centigrade for 0.2 hours. The resultant mixture was neutralized, phase separated and residual aniline was removed from the organic phase. The final product comprised methylene di(phenylamine) having 4,4'-, 2,4'- and 2,2'-isomer and polymeric amine.

The reduction of N-methyl MDA and acridane and acridine levels of the above product in comparison with that of methylene di(phenylamine) prepared by the conventional process (no reduction in acid level before digestion) was measured by gas chromatography as reported below.

|  | MDA of Example 1A | Conventional MDA |
|---|---|---|
| Reaction Conditions: | | |
| % by wt. acid at condensation | 0.195 | 0.100 |
| % by wt. acid at digestion | 0.100 | 0.100 |
| Content of Impurities: | | |
| N-methyl MDA content | 0.61% | 0.77% |
| Acridane/Acridine content | 0.05% | 0.07% |

Example 1B

In a properly equipped phosgenation reactor, the phosgenation of methylene di(phenylamine)final product of Example 1A was carried out in chlorobenzene with a 150% molar excess of phosgene by heating the reaction mixture to 120 degrees Centigrade. The resulting isocyanate material was dephosgenated and by fractional distillation and flash concentration chlorobenzene was removed and the product isocyanate was recovered by separation techniques.

Example 1C

The isocyanate product of Example 1C was evaluated by rating the absorptions of grey color (at 520 nm) in the ultra-violet visible spectrum. The lower the absorption value, the lighter the color. The color rating is believed to correlate with the content of impurities such as N-methyl MDA and acridane and acridine. The isocyanate product of the invention had a grey color rating 0.030 to 0.035. A grey color rating of 0.50 is typical of comparable isocyanate products derived from methylene di(phenylamine) which are not characterized by the the high temperature/low acid method of preparation as described herein. As would be realized, the method of this invention results in about 24% reduction in grey color. Products based on the isocyanate products showed a similar reduction in color.

Although the invention has been described in detail in the foregoing for the purpose of illustration, it is to be understood that the details are for that purpose and that variations can be made therein by those skilled in the art without departing from the spirit and scope of the invention except as may be limited by the claims.

What is claimed is:

1. A process for preparing a reaction product containing methylene di(phenylamine) comprising reacting aniline with an formaldehyde, in the presence of a low level of an acid which is sufficient to catalyze the reaction at an initial and/or condensation stage of said reaction and produce methylene di(phenylamine)intermediates; providing a reaction mixture at the condensation stage with an acid content which is at or below the initial acid level at the end of the condensation stage, and holding reaction mixture at a high temperature which is sufficient to effect a rearrangement of the intermediates to produce a reaction product containing methylene di(phenylamines) and low levels of impurities.

2. The process of claim 1 wherein the acid is hydrochloric acid.

3. The process of claim 1 wherein the low acid level is from 0.01 to 1.0 percent based on the weight of the reaction mixture.

4. The process of claim 1 wherein the acid level at the end of the condensation stage is at a low level.

5. The process of claim 1 wherein the acid content of the reaction mixture is reduced to a level below the level at the end of the condensation stage.

6. The process of claim 5 wherein the acid level is reduced to less than 1 percent by weight based on the weight of the reaction mixture.

7. The process of claim 1 wherein the acid level is reduced by partially neutralizing the reaction mixture with a base.

8. The process of claim 1 wherein the high temperature is in the range of 100 to 250 degrees Centigrade.

9. A reaction product comprising methylene di(phenylamine) which is prepared by the process of claim 1.

10. The reaction product of claim 9 which is characterized in that it contains low levels of impurities.

11. The reaction product of claim 9 which is characterized in that it contains low levels of N-methyl methylene di(phenylamine) and acridane and acridine.

12. A process for preparing an isocyanate product comprising phosgenating the product containing methylene di(phenylamine) as prepared in claim 1.

13. An isocyanate product which is prepared by the process of claim 12.

14. A process for preparing an isocyanate reaction product by reacting the isocyanate material of claim 13 with an active hydrogen containing material.

15. A process for preparing a foam comprising reacting the isocyanate material of claim 13 with an active hydrogen containing material in the presence of a blowing agent.

16. A foam which is prepared by the process of claim 15.

* * * * *